United States Patent
Vassiliades et al.

(10) Patent No.: US 9,138,228 B2
(45) Date of Patent: Sep. 22, 2015

(54) VASCULAR CONDUIT DEVICE AND SYSTEM FOR IMPLANTING

(75) Inventors: Thomas A. Vassiliades, Atlanta, GA (US); Ajit Yoganathan, Tucker, GA (US); Jorge Hernan Jimenez, Atlanta, GA (US)

(73) Assignees: Emory University, Atlanta, GA (US); Georgia Tech Research Institute, Atlanta, GA (US)

( * ) Notice: Subject to any disclaimer, the term of this patent is extended or adjusted under 35 U.S.C. 154(b) by 1794 days.

(21) Appl. No.: 11/251,100

(22) Filed: Oct. 14, 2005

(65) Prior Publication Data

US 2006/0089707 A1   Apr. 27, 2006

Related U.S. Application Data

(63) Continuation-in-part of application No. 10/915,691, filed on Aug. 11, 2004, now abandoned.

(51) Int. Cl.
*A61B 17/11* (2006.01)
*A61F 2/06* (2013.01)
(Continued)

(52) U.S. Cl.
CPC ............... *A61B 17/11* (2013.01); *A61F 2/064* (2013.01); *A61F 2/2493* (2013.01); *A61B 2017/00243* (2013.01); *A61B 2017/00252* (2013.01); *A61B 2017/1107* (2013.01); *A61B 2017/1135* (2013.01)

(58) Field of Classification Search
CPC ............. A61B 17/11; A61B 17/32053; A61B 2018/00392; A61B 2017/00247; A61B 2017/0237

USPC ................. 606/108, 151–154, 156; 623/1.23
See application file for complete search history.

(56) References Cited

U.S. PATENT DOCUMENTS 3,512,519 A   5/1970 Hall
3,540,451 A   11/1970 Zeman
(Continued)

FOREIGN PATENT DOCUMENTS

CA   2526920   2/2009
CN   1842354   10/2006
(Continued)

OTHER PUBLICATIONS

Guidant Heartstring; originally retrieved from <http://www.guidant.com/products>; presently retrieved from <http://web.archive.org/web/20031206212233/http://www.guidant.com/products/product-templates/cs/heartstring.shtml> dated 2003.
(Continued)

*Primary Examiner* — Dianne Dornbusch
*Assistant Examiner* — Michael Mendoza
(74) *Attorney, Agent, or Firm* — Alston & Bird LLP (57) ABSTRACT

The present invention provides a vascular conduit device including a deformable flange and complementary securing ring in cooperation for securing the device within an aperture defined in a tissue wall. The present invention further provides a system for implanting such a vascular conduit device in a tissue wall. More specifically, the present invention provides a system including a coring device for defining an aperture in a tissue wall (such as a ventricle and/or a blood vessel) and securely implanting a vascular conduit device therein so as to provide fluid communication between a first and second surface of the tissue wall via the vascular conduit device.

31 Claims, 8 Drawing Sheets

(51) Int. Cl.
*A61F 2/24* (2006.01)
*A61B 17/00* (2006.01)

(56) References Cited

U.S. PATENT DOCUMENTS

| | | | |
|---|---|---|---|
| 3,856,021 A | 12/1974 | McIntosh | |
| 4,336,819 A | 6/1982 | Nishihara | |
| 4,366,819 A | 1/1983 | Kaster | |
| 4,769,031 A | 9/1988 | McGough et al. | |
| 4,904,264 A | 2/1990 | Scheunemann | |
| 5,098,369 A | 3/1992 | Heilman et al. | |
| 5,129,913 A | 7/1992 | Ruppert | |
| 5,139,517 A | 8/1992 | Corral | |
| 5,158,563 A | 10/1992 | Cosman | |
| 5,222,980 A | 6/1993 | Gealow | |
| 5,256,160 A | 10/1993 | Clement | |
| 5,291,179 A | 3/1994 | Ooe et al. | |
| 5,447,533 A | 9/1995 | Vachon et al. | |
| 5,456,714 A | 10/1995 | Owen | |
| 5,577,993 A | 11/1996 | Zhu et al. | |
| 5,582,616 A | 12/1996 | Bolduc et al. | |
| 5,695,504 A | 12/1997 | Gifford et al. | |
| 5,755,697 A | 5/1998 | Jones et al. | |
| 5,782,844 A | 7/1998 | Yoon et al. | |
| 5,810,836 A | 9/1998 | Hussein et al. | |
| 5,810,851 A | 9/1998 | Yoon | |
| 5,814,005 A | 9/1998 | Barra et al. | |
| 5,824,070 A | 10/1998 | Jarvik | |
| 5,824,071 A | 10/1998 | Nelson et al. | |
| 5,827,316 A | 10/1998 | Young et al. | |
| 5,843,088 A | 12/1998 | Barra et al. | |
| 5,893,369 A | 4/1999 | LeMole | |
| 5,910,153 A | 6/1999 | Mayenberger | |
| 5,924,424 A | 7/1999 | Stevens et al. | |
| 5,944,730 A * | 8/1999 | Nobles et al. | 606/151 |
| 5,976,174 A | 11/1999 | Ruiz | |
| 5,984,956 A | 11/1999 | Tweden et al. | |
| 5,989,278 A * | 11/1999 | Mueller | 606/180 |
| 6,001,056 A | 12/1999 | Jassawalla et al. | |
| 6,007,576 A * | 12/1999 | McClellan | 623/23.64 |
| 6,022,324 A | 2/2000 | Skinner | |
| 6,022,367 A | 2/2000 | Sherts | |
| 6,039,748 A | 3/2000 | Savage et al. | |
| 6,066,085 A | 5/2000 | Heilman et al. | |
| 6,079,414 A | 6/2000 | Roth | |
| 6,080,173 A | 6/2000 | Williamson, IV et al. | |
| 6,080,176 A | 6/2000 | Young | |
| 6,146,325 A | 11/2000 | Lewis et al. | |
| 6,241,743 B1 * | 6/2001 | Levin et al. | 606/153 |
| 6,254,564 B1 | 7/2001 | Wilk et al. | |
| 6,267,732 B1 | 7/2001 | Heneveld et al. | |
| 6,273,862 B1 | 8/2001 | Privitera et al. | |
| 6,290,728 B1 | 9/2001 | Phelps et al. | |
| 6,346,071 B1 | 2/2002 | Mussivand | |
| 6,390,976 B1 | 5/2002 | Spence et al. | |
| 6,401,720 B1 | 6/2002 | Stevens et al. | |
| 6,409,739 B1 | 6/2002 | Nobles et al. | |
| 6,443,957 B1 | 9/2002 | Addis | |
| 6,458,140 B2 * | 10/2002 | Akin et al. | 606/153 |
| 6,537,300 B2 | 3/2003 | Girton | |
| 6,551,319 B2 | 4/2003 | Lieberman | |
| 6,551,332 B1 | 4/2003 | Nguyen et al. | |
| 6,589,277 B1 | 7/2003 | Fabiani et al. | |
| 6,607,541 B1 | 8/2003 | Gardiner et al. | |
| 6,638,237 B1 | 10/2003 | Guiles et al. | |
| 6,651,670 B2 | 11/2003 | Rapacki et al. | |
| 6,669,708 B1 * | 12/2003 | Nissenbaum et al. | 606/153 |
| 6,673,043 B1 | 1/2004 | Landesberg | |
| 6,676,678 B2 | 1/2004 | Gifford, III et al. | |
| 6,689,147 B1 | 2/2004 | Koster, Jr. | |
| 6,695,859 B1 | 2/2004 | Golden et al. | |
| 6,699,256 B1 | 3/2004 | Logan et al. | |
| 6,705,988 B2 | 3/2004 | Spence et al. | |
| 6,726,648 B2 | 4/2004 | Kaplon et al. | |
| 6,732,501 B2 | 5/2004 | Yu et al. | |
| 6,740,101 B2 * | 5/2004 | Houser et al. | 606/153 |
| 6,776,787 B2 | 8/2004 | Phung et al. | |
| 6,802,806 B2 | 10/2004 | McCarthy et al. | |
| 6,808,498 B2 | 10/2004 | Laroya et al. | |
| 6,824,071 B1 | 11/2004 | McMichael | |
| 6,827,683 B2 * | 12/2004 | Otawara | 600/123 |
| 6,863,677 B2 | 3/2005 | Breznock | |
| 6,942,672 B2 | 9/2005 | Heilman et al. | |
| 6,984,241 B2 | 1/2006 | Lubbers et al. | |
| 6,994,666 B2 | 2/2006 | Shannon et al. | |
| 7,018,384 B2 | 3/2006 | Skakoon | |
| 7,033,372 B1 | 4/2006 | Cahalan | |
| 7,048,681 B2 | 5/2006 | Tsubouchi et al. | |
| 7,056,286 B2 | 6/2006 | Ravenscroft et al. | |
| 7,077,801 B2 | 7/2006 | Haverich | |
| 7,083,631 B2 * | 8/2006 | Houser et al. | 606/153 |
| 7,182,771 B1 | 2/2007 | Houser et al. | |
| 7,214,234 B2 * | 5/2007 | Rapacki et al. | 606/167 |
| 7,232,421 B1 | 6/2007 | Gambale et al. | |
| 7,258,694 B1 | 8/2007 | Choi et al. | |
| 7,309,343 B2 | 12/2007 | Vargas et al. | |
| 7,331,956 B2 | 2/2008 | Hovda et al. | |
| 7,404,792 B2 | 7/2008 | Spence et al. | |
| 7,510,561 B2 | 3/2009 | Beane et al. | |
| 7,637,919 B2 * | 12/2009 | Ishikawa et al. | 606/153 |
| 7,717,844 B2 | 5/2010 | Cohn | |
| 7,744,527 B2 | 6/2010 | Cohn | |
| 7,766,811 B2 | 8/2010 | Haverich | |
| 7,799,041 B2 | 9/2010 | Beane et al. | |
| 7,842,068 B2 | 11/2010 | Ginn | |
| 7,846,123 B2 | 12/2010 | Vassiliades et al. | |
| 7,846,179 B2 | 12/2010 | Belef et al. | |
| 7,931,581 B2 | 4/2011 | Cohn | |
| 7,942,805 B2 | 5/2011 | Shambaugh, Jr. | |
| 7,993,392 B2 | 8/2011 | Righini et al. | |
| 8,226,670 B2 | 7/2012 | Beane et al. | |
| 8,430,836 B2 | 4/2013 | Vassiliades et al. | |
| 8,556,930 B2 | 10/2013 | Ellingwood | |
| 8,579,790 B2 | 11/2013 | Jeffery et al. | |
| 2001/0051809 A1 | 12/2001 | Houser et al. | |
| 2002/0019623 A1 | 2/2002 | Altman et al. | |
| 2002/0019643 A1 | 2/2002 | Gifford et al. | |
| 2002/0032462 A1 | 3/2002 | Houser et al. | |
| 2002/0038127 A1 | 3/2002 | Blatter et al. | |
| 2002/0045846 A1 | 4/2002 | Kaplon et al. | |
| 2002/0058958 A1 | 5/2002 | Walen | |
| 2002/0095210 A1 | 7/2002 | Finnegan et al. | |
| 2002/0099394 A1 | 7/2002 | Houser et al. | |
| 2002/0116018 A1 * | 8/2002 | Stevens et al. | 606/153 |
| 2002/0177865 A1 | 11/2002 | McIntosh | |
| 2002/0193806 A1 | 12/2002 | Moenning et al. | |
| 2003/0023255 A1 | 1/2003 | Miles et al. | |
| 2003/0040765 A1 | 2/2003 | Breznock | |
| 2003/0045834 A1 | 3/2003 | Wing et al. | |
| 2003/0078592 A1 | 4/2003 | Heilman et al. | |
| 2003/0130668 A1 | 7/2003 | Nieman et al. | |
| 2003/0181843 A1 * | 9/2003 | Bibber et al. | 604/8 |
| 2004/0002624 A1 | 1/2004 | Yu et al. | |
| 2004/0050393 A1 | 3/2004 | Golden et al. | |
| 2004/0068299 A1 | 4/2004 | Laske et al. | |
| 2004/0077989 A1 | 4/2004 | Goode et al. | |
| 2004/0092858 A1 | 5/2004 | Wilson et al. | |
| 2004/0097973 A1 * | 5/2004 | Loshakove et al. | 606/144 |
| 2004/0098011 A1 | 5/2004 | Vargas et al. | |
| 2004/0133155 A1 | 7/2004 | Varner et al. | |
| 2004/0153112 A1 | 8/2004 | Nissenbaum et al. | |
| 2004/0162608 A1 | 8/2004 | Haverich | |
| 2004/0167547 A1 | 8/2004 | Beane et al. | |
| 2004/0171905 A1 | 9/2004 | Yu et al. | |
| 2004/0186490 A1 | 9/2004 | Gifford et al. | |
| 2004/0236170 A1 * | 11/2004 | Kim | 600/16 |
| 2005/0033107 A1 | 2/2005 | Tsubouchi | |
| 2005/0043781 A1 | 2/2005 | Foley | |
| 2005/0075656 A1 | 4/2005 | Beaupre | |
| 2005/0101982 A1 | 5/2005 | Ravenscroft et al. | |
| 2005/0101983 A1 | 5/2005 | Loshakove et al. | |
| 2005/0131451 A1 | 6/2005 | Kleshinski et al. | |
| 2005/0137609 A1 | 6/2005 | Guiraudon | |
| 2005/0149093 A1 | 7/2005 | Pokorney | |

(56) References Cited

U.S. PATENT DOCUMENTS

| | | |
|---|---|---|
| 2005/0154411 A1 | 7/2005 | Breznock et al. |
| 2005/0171479 A1 | 8/2005 | Hruska et al. |
| 2005/0187568 A1 | 8/2005 | Klenk et al. |
| 2005/0192604 A1 | 9/2005 | Carson et al. |
| 2005/0209502 A1 | 9/2005 | Schmid et al. |
| 2005/0251187 A1 | 11/2005 | Beane et al. |
| 2006/0020326 A9 | 1/2006 | Bolduc et al. |
| 2006/0036313 A1 | 2/2006 | Vassiliades |
| 2006/0074484 A1 | 4/2006 | Huber |
| 2006/0089707 A1 | 4/2006 | Vassiliades et al. |
| 2006/0099716 A1 | 5/2006 | Tipler et al. |
| 2006/0142634 A1 | 6/2006 | Anstadt et al. |
| 2006/0161193 A1 | 7/2006 | Beane et al. |
| 2006/0167333 A1 | 7/2006 | Moore et al. |
| 2006/0241659 A1 | 10/2006 | Tulleken et al. |
| 2006/0259050 A1 | 11/2006 | De Winter |
| 2007/0055357 A1 | 3/2007 | Pokorney et al. |
| 2007/0066943 A1 | 3/2007 | Prasad et al. |
| 2007/0088375 A1 | 4/2007 | Beane et al. |
| 2007/0100363 A1 | 5/2007 | Dollar et al. |
| 2007/0106315 A1 | 5/2007 | Gregoric et al. |
| 2007/0106328 A1 | 5/2007 | Wardle et al. |
| 2007/0167968 A1 | 7/2007 | Pandey |
| 2007/0167969 A1 | 7/2007 | Pandey |
| 2007/0173879 A1 | 7/2007 | Pandey |
| 2007/0197856 A1 | 8/2007 | Gellman et al. |
| 2007/0265643 A1* | 11/2007 | Beane et al. .................. 606/153 |
| 2008/0004640 A1 | 1/2008 | Ellingwood |
| 2008/0009668 A1 | 1/2008 | Cohn |
| 2008/0009887 A1 | 1/2008 | Cohn |
| 2008/0009891 A1 | 1/2008 | Cohn |
| 2008/0039883 A1 | 2/2008 | Nohilly |
| 2008/0058846 A1 | 3/2008 | Vosough |
| 2008/0076959 A1 | 3/2008 | Farnan et al. |
| 2008/0161826 A1 | 7/2008 | Guiraudon |
| 2008/0177301 A1 | 7/2008 | Svensson |
| 2008/0255597 A1 | 10/2008 | Pravong et al. |
| 2009/0012552 A1 | 1/2009 | Pandey et al. |
| 2009/0082778 A1 | 3/2009 | Beane et al. |
| 2009/0112062 A1 | 4/2009 | Bakos |
| 2009/0204206 A1 | 8/2009 | Parquet et al. |
| 2010/0004739 A1 | 1/2010 | Vesely |
| 2010/0010500 A1 | 1/2010 | Beane et al. |
| 2010/0087907 A1 | 4/2010 | Lattouf |
| 2010/0161040 A1 | 6/2010 | Braido et al. |
| 2010/0168778 A1 | 7/2010 | Braido |
| 2011/0118833 A1 | 5/2011 | Reichenbach et al. |
| 2011/0144680 A1 | 6/2011 | Nguyen et al. |
| 2012/0089181 A1 | 4/2012 | Shanley et al. |
| 2013/0218169 A1 | 8/2013 | Vassiliades et al. |
| 2014/0039375 A1 | 2/2014 | Jimenez et al. |
| 2014/0194833 A1 | 7/2014 | Andrus |

FOREIGN PATENT DOCUMENTS

| | | |
|---|---|---|
| EP | 1 669 042 A2 | 6/2006 |
| EP | 1691884 | 3/2011 |
| EP | 1628702 | 5/2013 |
| EP | 1706168 | 11/2013 |
| JP | 11500642 | 1/1999 |
| JP | 2002518082 | 6/2002 |
| JP | 2006518624 | 8/2006 |
| JP | 2007510522 | 4/2007 |
| WO | 9325148 | 12/1993 |
| WO | 9625886 | 8/1996 |
| WO | WO 97/13463 | 4/1997 |
| WO | 9965409 | 12/1999 |
| WO | 0000193 | 1/2000 |
| WO | WO 00/15147 | 3/2000 |
| WO | WO 00/15149 | 3/2000 |
| WO | 0041759 | 7/2000 |
| WO | 0074747 | 12/2000 |
| WO | 03001980 | 1/2003 |
| WO | 2004026147 | 4/2004 |
| WO | 2004096059 | 11/2004 |
| WO | 2005046783 | 5/2005 |
| WO | 2006019755 | 2/2006 |
| WO | 2006020651 | 2/2006 |
| WO | 2006093970 | 9/2006 |
| WO | 2007038109 | 4/2007 |
| WO | 2007047212 | 4/2007 |
| WO | 2007117612 | 10/2007 |
| WO | 2008131453 | 10/2008 |
| WO | 2008153872 | 12/2008 |
| WO | 2009100198 | 8/2009 |
| WO | 2012040233 | 3/2012 |
| WO | 2012103546 | 8/2012 |
| WO | 2012106422 | 8/2012 |
| WO | 2013064529 | 5/2013 |

OTHER PUBLICATIONS

International Preliminary Report on Patentability for Application No. PCT/US2005/028291; dated Mar. 3, 2009.
International Search Report and Written Opinion for Application No. PCT/US2005/028291; dated May 28, 2008.
International Preliminary Report on Patentability for Application No. PCT/US2006/039435; dated Apr. 16, 2008.
International Search Report and Written Opinion for Application No. PCT/ US2006/039435; dated Feb. 6, 2007.

* cited by examiner

VASCULAR CONDUIT DEVICE AND SYSTEM FOR IMPLANTING

CROSS-REFERENCE TO RELATED APPLICATIONS

This application is a continuation-in-part of copending U.S. patent application Ser. No. 10/915,691, filed on Aug. 11, 2004, now abandoned, which is hereby incorporated herein in its entirety by reference.

FIELD OF INVENTION

This invention relates to devices and methods for creating and maintaining a fluid conduit in a tissue wall. For example, some embodiments of the present invention may provide an alternative conduit between the left ventricle and the aorta to create a double-outlet left ventricle.

BACKGROUND OF THE INVENTION

Construction of an alternative conduit between the left ventricle and the aorta (an apicoaortic conduit, or AAC) to create a double-outlet left ventricle (LV) has been successfully employed to treat a variety of complex congenital LV outflow obstruction (fibrous tunnel obstruction, aortic annular hypoplasia, tubular hypoplasia of the ascending aorta, and patients with diffuse septal thickening, severe LV hypertrophy and a small LV cavity) as well as adult-onset aortic stenosis in patients with complicating preoperative conditions (previous failed annular augmentation procedures, previous infection, previous CABG with patent anterior internal mammary artery grafts, and a porcelain ascending aorta).

However, the AAC insertion procedure has been poorly accepted, primarily because of early valve failures using first-generation bioprostheses as well as the success of direct LVOTO repair and aortic valve replacement. In the United States, despite an aging population, the unadjusted mortality for isolated aortic valve operations in 2001 remained under 4%. Further, the AAC insertion operation, with or without cardiopulmonary bypass, has not been as technically straightforward as direct aortic valve replacement. For most surgeons, AAC insertion is not a familiar operation and is of historical interest only.

Nonetheless, several studies have demonstrated that AAC insertion successfully lessens the LV-aortic pressure gradient, preserves or improves ventricular function and maintains normally distributed blood flow through the systemic and coronary circulation. While there have been several techniques described, the most commonly employed method is the lateral thoracotomy approach with placement of the AAC to the descending aorta. Other techniques include a median sternotomy approach with insertion of the distal limb of the AAC to the ascending aorta, to the transverse part of the aortic arch, or to the intra-abdominal supraceliac aorta.

In general, the thoracic aorta and the left ventricle apex are exposed through a left lateral thoracotomy, and a needle is passed through the apex and into the left ventricle. While the connector is still spaced apart from the apex, the sutures that will fix the connector to the apex are threaded through a cuff on the connector and through the apex in a matching pattern. The cuff is set back from the end of the connector by 1-2 centimeters to allow the end of the connector to extend through the heart muscle and into the left ventricle. Once the sutures are in place, a ventricular coring device is used to remove a core of ventricular muscle, and the pre-threaded sutures are then pulled to draw the connector into the opening until the cuff comes to rest on the apex. The sutures are tied off, and additional sutures may be added. Either before or after this procedure, the opposite end of the connector is attached to a valved conduit which terminates at the aorta.

The current techniques and technology available to perform AAC insertion were originally designed to be performed on-pump; either with an arrested or fibrillating heart. While off-pump cases have been described, they can be technically difficult due to the shortcomings of presently available vascular conduits and systems for installing such conduits. For example, because existing conduits require the use of sutures to reliably secure the connector in place, it is often difficult for surgeons or other clinicians to insert such sutures reliably in active cardiac and/or vascular tissue.

SUMMARY OF THE INVENTION

This invention describes an improved system and method for the insertion of a vascular conduit (such as an AAC) that will significantly improve and simplify the in vivo insertion of a graft into the beating cardiac apex or other tissue walls (such as other areas of the heart including the anterior, lateral, posterior walls of the left or right ventricle, the left or right atrium, the aortic wall, ascending, transverse, or descending, or other blood vessel walls), such that vascular conduit insertions (including AAC procedures) may be rendered far more attractive to clinicians. Because vascular conduits and systems of the present invention may be used to create alternate outflow tracts in "off-pump" procedures, the embodiments of the present invention may effectively reduce and/or negate the detrimental effects of both cardio-pulmonary by-pass (CPB) and global cardiac ischemia. Additionally, because some conduit embodiments of the present invention (for AAC procedures, for example) may be inserted into a ventricular or atrial free wall or cardiac apex, the conduction system of the heart may be avoided, along with the native coronary arteries and grafts from previous surgical revascularization. In some embodiments of the present invention, wherein the system is used to implant an AAC, a small size valve (19 to 21 mm for typical adult body surface areas) is usually adequate; as the effective postoperative orifice is the sum of the native and prosthetic aortic valves. Further, the present invention provides vascular conduits that may be compatible with newer generation biologic valves, such that valved conduit failure is far less likely.

In one embodiment, the present invention provides a system for implanting a vascular conduit device (such as an AAC component). According to some embodiments, the system comprises a coring device for defining an aperture in a tissue wall (such as a cardiac free wall or apex and/or the aorta) having a first tissue surface and a second tissue surface. The coring device may define a lumen adapted to be capable of receiving a guide wire for directing the coring device to the first or second tissue surface, depending upon whether the approach is intra- or extra-vascular, respectively. The system may also comprise a conduit device for lining the aperture defined in the tissue wall and maintaining fluid communication between the first and second tissue surfaces of the tissue wall. The conduit device may be adapted to be capable of being advanced over the guide wire and/or the coring device so as to be guided to the aperture defined by the coring device. The conduit device may comprise, in some embodiments: a tube having proximal and distal ends, and inside and outside surfaces; a flexible flange disposed at or near the distal end, wherein the flexible flange is adapted to be capable of operably engaging the first tissue surface; and a securing ring adapted to fit over the tube and adapted to be capable of operably engaging the second tissue surface and cooperating with the flexible flange so as to secure the conduit device within the aperture.

According to some embodiments of the present invention, the system may also comprise a hemostatic device for selectively deploying so as to temporarily occlude the aperture (so as to prevent the passage of blood through the aperture and into an adjacent body cavity, for example). The hemostatic device may also be adapted to be capable of being advanced over the guide wire and/or within the lumen of the coring device such that the hemostatic device may be accurately guided to the site of the newly-formed aperture created by the coring device. The hemostatic device may comprise at least one of an "umbrella" occlusion device, a dilation balloon, and/or combinations of such devices. Furthermore, according to various system embodiments of the present invention, the coring device may comprise at least one of: a pulsed laser scalpel; a continuous wave laser scalpel; a mechanical coring device; a device employing ultrasonic energy (such as high-frequency focused ultra-sound); and/or combinations of such coring devices. Some embodiments of the present invention may also provide a specialized delivery device for enclosing the conduit device and selectively implanting the conduit device within the aperture. The delivery device may be operably engaged with an outer surface of the coring device and may comprise one or more retracting arms for dilating the aperture prior to and/or simultaneously with the implantation of the conduit device.

Some additional system embodiments of the present invention may also comprise a guiding catheter defining a guiding lumen for receiving and directing the coring device and the conduit device to the tissue wall via an endovascular pathway. Thus, according to various system embodiments of the present invention, the system may be used to implant the conduit device via an endovascular pathway such that the conduit may be implanted from inside the left ventricle and/or inside another blood vessel.

Other embodiments of the present invention provide a vascular conduit device for lining an aperture defined in a tissue wall (such as the cardiac wall, apex and/or a blood vessel wall) and maintaining fluid communication between a first tissue surface and a second tissue surface of the tissue wall. According to some embodiments, the vascular conduit device may comprise a tube having proximal and distal ends, and inside and outside surfaces, wherein the outside surface of the tube defines a plurality of ridges. The vascular conduit device may further comprise a flexible flange disposed at or near the distal end for operably engaging the first tissue surface and a securing ring adapted to fit over the tube for operably engaging the second tissue surface. The securing ring may also comprise at least one deformable pawl member for releasably engaging the plurality of ridges defined by the outer surface of the tube such that the securing ring cooperates with the flexible flange so as to secure the vascular conduit device within the aperture.

According to some embodiments, the flexible flange and/or securing ring may define complementary concave and/or convex profiles so as to conform more completely to the first and second tissue surfaces. Furthermore, the flexible flange may comprise a frusto-conical assembly such that the flange may be more easily inserted into the aperture. According to various other embodiments of the present invention, the outside surface of the tube may comprise threading on at least a portion of the outside surface of the tube and corresponding threading on an inside diameter of the securing ring such that the securing ring may be secured with respect to the flange and the tissue wall held there between.

According to some embodiments of the present invention, the flexible flange may be soft and thin enough to bend backwards so that it can be pushed through the aperture defined in the tissue wall, but rigid enough to flex back to its original position and hold its shape once it emerges along a first tissue surface of the tissue wall. The tube of the vascular conduit device may then be drawn back so that the flexible flange presses against the first tissue surface of the tissue wall. The securing ring may then be deployed over the body of the connector and against the second tissue surface of the tissue wall. Various vascular conduit device embodiments are described herein to secure the position of the second ring against a surface of the tissue wall such that no sutures may be required. Such embodiments may include, but are not limited to: the ridge and pawl mechanism described above, a threaded surfaces disposed on the tube and an inner surface of the securing ring, a biasing device for biasing the securing ring toward the flange; and/or combinations of such securing devices.

According to one embodiment for using the new system and/or vascular conduit device of the present invention, a needle is passed through a tissue wall (such as the wall of the cardiac apex) to provide access to the first tissue surface (defining the interior of the left ventricle, for example). A guide wire may then be inserted into the opening and, following dilation of the opening, an occlusion device may be threaded over the wire and into a cavity defined by the tissue wall and deployed. A coring device may then be threaded in-line over the guide wire such that a core of tissue may be removed to form an aperture in the tissue wall. While the occlusion device maintains hemostasis, the coring device may be removed and the vascular conduit device of the present invention may be mounted on a dilator and introduced over the guide wire and occlusion device catheter. As the vascular conduit device is introduced into the aperture, the flexible flange retracts. Furthermore, as discussed above, as the vascular conduit device enters the aperture, it may displace the occlusion device to allow the flange to resume its normal shape. As discussed above, the vascular conduit device may then be drawn tight against the first tissue wall such that the securing ring may be deployed over the body of the vascular conduit device to fit snugly against the second tissue surface. Once the connector is firmly in place, the occlusion device may be withdrawn and the vascular conduit device may be clamped shut while its free end is connected to a vascular graft or valved conduit that may terminate at another tissue wall (such as a blood vessel wall, for example).

Use of this new vascular conduit device, system, and method will significantly improve the ease and safety of vascular conduit insertion (such as the implantation of AAC devices). As persons of ordinary skill would readily appreciate, this method can also be, used in a minimally invasive, endoscopically assisted approach.

BRIEF DESCRIPTION OF THE DRAWINGS

The invention will be better understood by reference to the Detailed Description of the Invention when taken together with the attached drawings, wherein.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. The singular forms "a," "an," and "the" include plural referents unless the context clearly dictates otherwise.

Although some embodiments of the invention described herein are directed to a vascular conduit device 100 and a system for implanting such a device to form an apico-aortic connector (AAC) between the cardiac apex and the aorta, it will be appreciated by one skilled in the art that the invention is not so limited. For example, aspects of the vascular conduit device 100 and systems of the present invention can also be used to establish and/or maintain conduits in a variety of tissue structures using minimally-invasive and/or invasive delivery techniques. Furthermore, while the embodiments of the invention described herein are directed to the thoracoscopic implantation of the vascular conduit device to form at least one vascular port for establishing an AAC, it should be understood that the system and/or vascular conduit device embodiments of the present invention may be used to establish valved and/or open conduits (including bypass conduits) to augment native blood vessels in order to treat a variety of vascular conditions including, but not limited to: aortic valvular disease, congestive heart failure, left ventricle outflow tract obstructions (LVOTO), peripheral arterial obstructions, small vessel obstructions, and/or other conditions. Furthermore, the vascular conduit device and system of the present invention may also be used to establish a port for inter-ventricular repairs such as, for example, valve repair and/or replacement or ablation procedures. Thus, the vascular conduit device 100 described in further detail below may also comprise a threaded fluid-tight cap, and/or a cap having at least one pawl member (for engaging corresponding ridges defined on an outer surface of the vascular conduit device 100) for selectively sealing the proximal end 7 of the vascular conduit device 100 such that the tube 1 may serve as a re-usable port for repairing and/or treating diseased portions of the cardiac anatomy. Furthermore, the vascular conduit device 100 and system embodiments of the present invention may also be used to implant a conduit and/or port for left ventricular assist devices.

Figure 12:
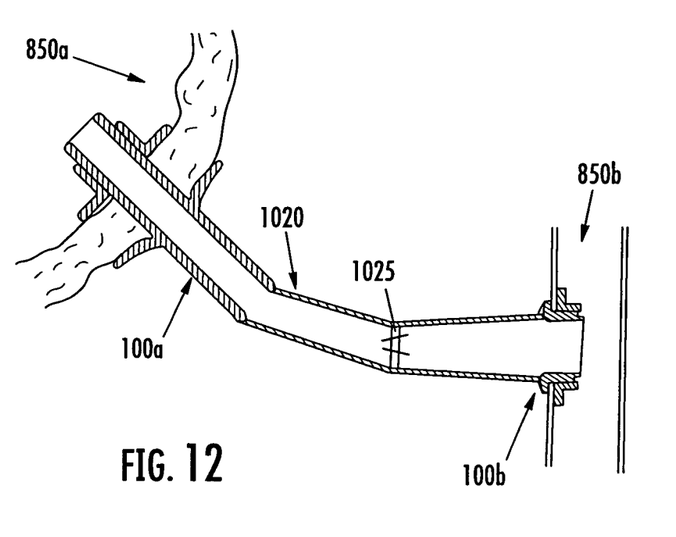
FIG. 12 is a cross-sectional side view of an exemplary apico-aortic connection (AAC) inserted via endovascular methods using system embodiments of the present invention.

Furthermore, (as shown generally in FIG. 12) some system embodiments of the present invention may also be used "from the inside out", such that the coring device 830 and conduit device 100 may be passed from through an intravascular space (percutaneously). For example, in one possible embodiment, the system embodiments of the present invention may be used to establish an apico-aortic conduit (AAC) percutaneously (see FIG. 12). The system components may be introduced (via methods that will be appreciated by one skilled in the art) into the femoral vein, across the atrial septum, through the mitral valve and out the ventricular free wall. Therefore, the ventricular conduit device (see element 100a, FIG. 12) would be placed from inside the vasculature (via a guiding catheter, for example). In similar fashion, the aortic conduit device (see element 100b, FIG. 12) may be passed retrograde in the femoral artery (via guide wire and/or guiding catheter) or other blood vessel and implanted using the systems of the present invention from the luminal side of the aorta. The two connectors would then be joined with a valved conduit introduced from either end of the system (see FIG. 12).

Figure 1:
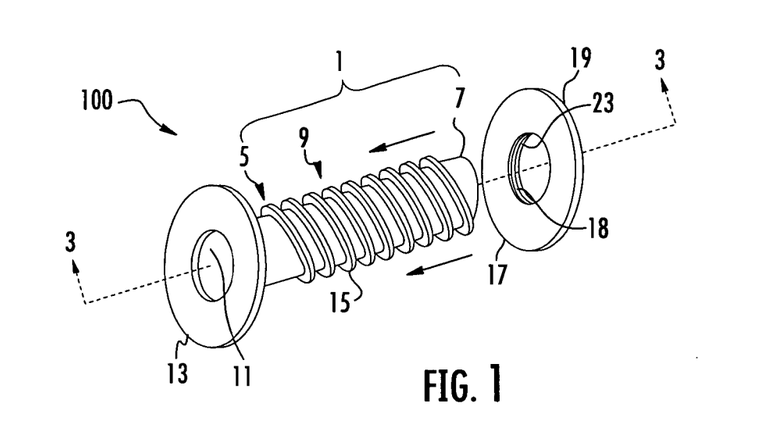
FIG. 1 is a perspective view of a first embodiment of an LV apical connector according to the invention.
Figure 2:
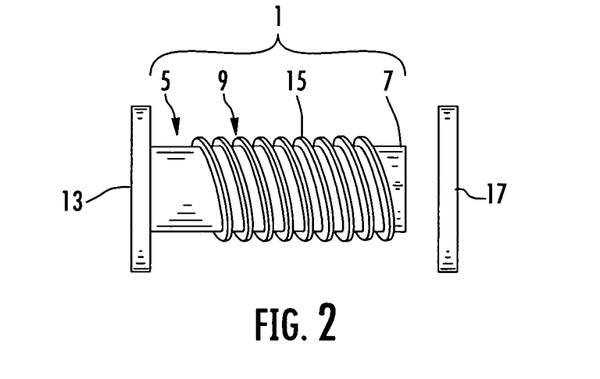
FIG. 2 is a side view of the embodiment shown in FIG. 1.

As shown in FIGS. 1 and 2, the vascular conduit device 100 according to one embodiment of the present invention includes tube (or conduit) 1 having an axis 3, distal end 5, a proximal end 7, an outer surface 9 and an inner surface 11. Distal end 5 is provided with a flange 13 extending, from outer surface 9 in a direction away from axis 3. Flange 13 may be integrally formed with tube 1, or it maybe formed separately and permanently attached to distal end 5 of tube 1 by known means. Tube 1 should be sufficiently rigid to maintain its shape so as not to occlude the passage of blood and/or other fluids therethrough during use (see generally, element 860, FIG. 8B). Flange 13 may be sufficiently flexible to allow introduction of the distal end 5 of the vascular conduit device 100 into an aperture 800 (see FIG. 8A) having a diameter equal to or slightly less than the diameter of outer surface 9, but have sufficient stiffness and/or shape memory to flex back to its original position once it has passed through the aperture 800 (which may be defined in a tissue wall 850, as shown generally in FIGS. 8A-8B).

Figure 6:
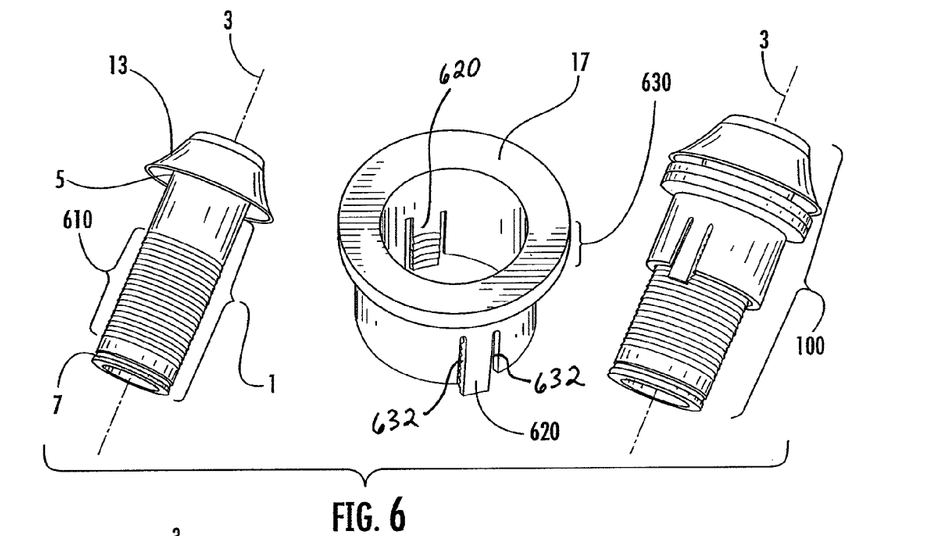
FIG. 6 is a perspective view of a vascular conduit device, including a tube, flexible flange, and securing ring, according to one embodiment of the present invention.
Figure 7:
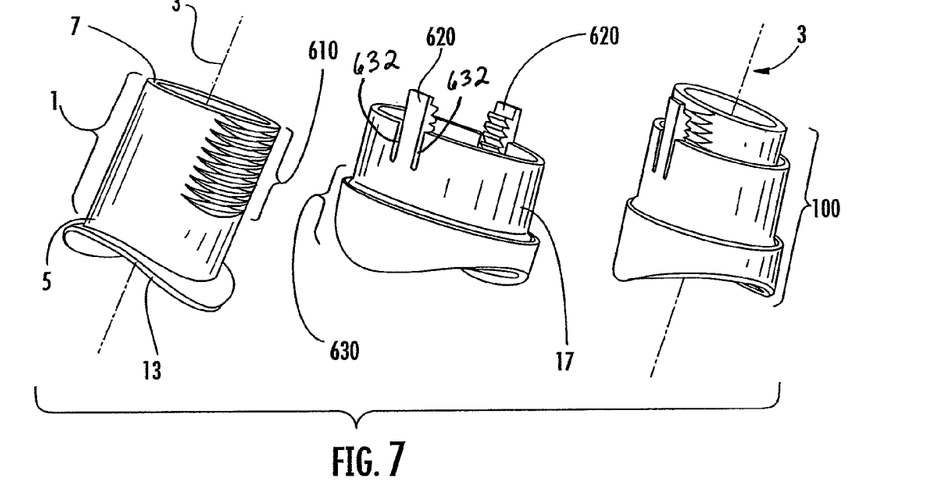
FIG. 7 is a perspective view of a vascular conduit device, including a tube, flexible flange, and securing ring, according to one embodiment of the present invention, wherein the flexible flange and securing rings define convex and concave profiles, respectively.
Figure 8A:
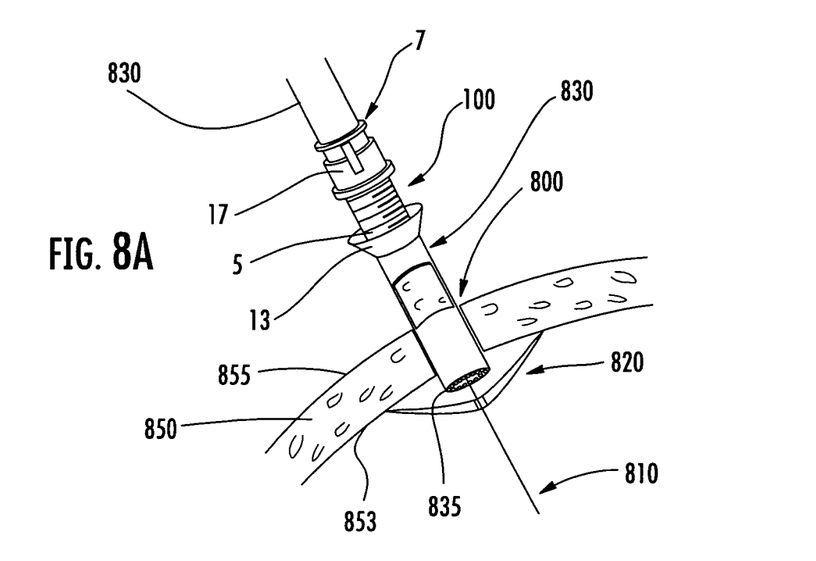
FIG. 8A is a cross-sectional view of a tissue wall and aperture defined therein in relation to one system embodiment of the present invention including a coring device for defining an aperture and a vascular conduit device for defining and maintaining the aperture.
Figure 8B:
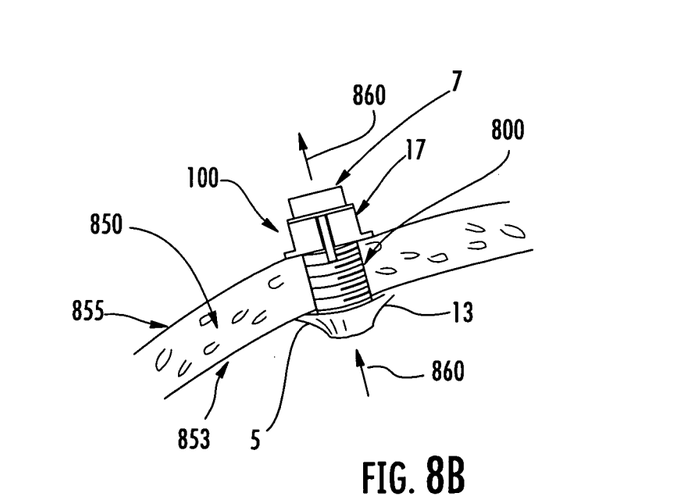
FIG. 8B is a cross-sectional view of a tissue wall and aperture defined therein including a side view of a vascular conduit device, according to one embodiment of the present invention, implanted in the aperture.

As shown generally in FIGS. 8A-8B, the vascular conduit device 100 may maintain and/or provide a lining for an aperture 800 defined in a tissue wall 850 so as to maintain fluid communication 860 between a first tissue surface 853 and a second tissue surface 855 of the tissue wall 850. As described generally above, and as shown in FIGS. 6 and 7, the vascular conduit device 100 may comprise a tube 1 having proximal 7 and distal 5 ends, and inside and outside surfaces, wherein the outside surface of the tube 1 defines a plurality of ridges 610. According to some embodiments, the vascular conduit device 100 may also comprise a flexible flange 13 disposed at or near the distal end 5 for operably engaging the first tissue surface 853 (see FIG. 8B). As shown in FIGS. 6 and 7, the vascular conduit device 100 may also comprise a securing ring 17 adapted to fit over the tube 1 and having a flange 630 for operably engaging the second tissue surface 855. The securing ring 17 may also comprise at least one deformable pawl member 620 for releasably engaging the plurality of ridges 610 defined by the outer surface of the tube 1 such that the securing ring 17 cooperates with the flexible flange 13 so as to secure the vascular conduit device 100 within the aperture 800. In one embodiment, the securing ring 17 comprises a flange 630 configured to engage the second tissue surface 855, and the deformable pawl member 620 extends axially along the axis 3 of the tube 1 at an opposite end of the flange. According to one aspect, the securing ring 17 has a wall thickness, and the deformable pawl member is defined by a pair of slots 632 formed through the wall thickness as shown in FIGS. 6 and 7.

Figure 10:
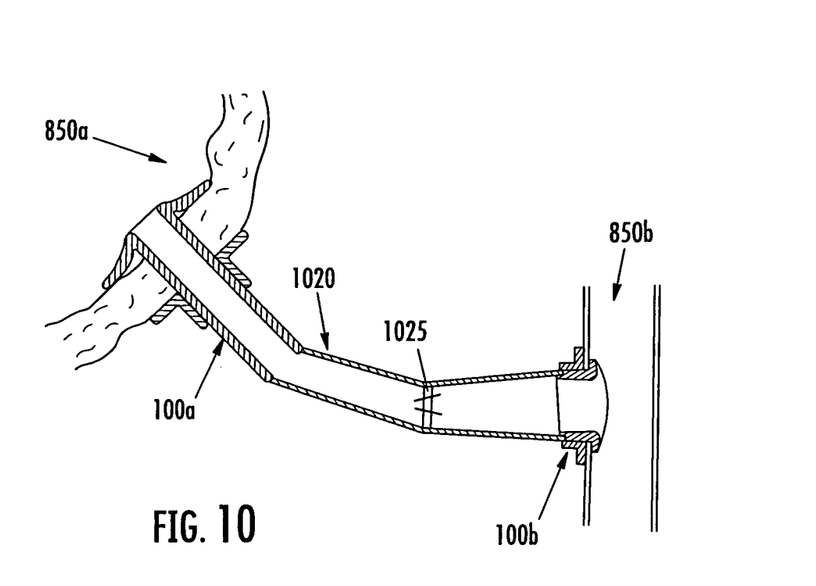
FIG. 10 is a cross-sectional side view of an exemplary apico-aortic connection (AAC) constructed using some embodiments of the present invention.

As shown generally in FIG. 8B, once the vascular conduit device 100 is secured within the aperture 800 defined in the tissue wall 850, the vascular conduit device 100 may define a pathway for fluid communication (and/or a pathway for thoracoscopic instruments or other surgical tools) between a first tissue surface 853 and a second tissue surface 855. Furthermore, the proximal end 7 of the vascular conduit device 100 may be configured to receive a number of different valved and/or open conduits for creating, for example, vascular bypasses or other alternate fluid pathways within a living organism. For example, according apico-aortic conduit embodiments of the present invention (see FIG. 10), a first vascular conduit device 100a (shown generally in FIG. 6) may be implanted and/or secured in the apex 850a of the left ventricle, and a second vascular conduit device 100b (shown generally in FIG. 7) may be implanted and/or secured within a wall 850b of the aorta. The two devices may then be connected via a commercially-available valved conduit device 1020 (including a one-way valve 1025) in order to create an alternative valved pathway for blood in order to augment a diminished flow of blood that may be passing through a diseased and/or damaged aortic valve. Thus, according to some embodiments, the proximal end 7 of the tube 1 defining the fluid pathway through the vascular conduit device 100 may be formed so as to be compatible with one or more existing valved conduit devices 1020. Furthermore, according to some embodiments, the vascular conduit device 100 may be fitted with an adapter sleeve (not shown) such that the proximal end 7 of the tube may be connected in a fluid-tight manner with one or more commercially-available conduit devices 1020 for establishing a bypass and/or alternate pathway between two body cavities or blood vessels. Furthermore, the vascular conduit device 100 of the present invention may be used to bypass and/or repair a variety of diseased and/or damaged blood vessels. For example, some embodiments of the present invention may be used to bypass an abdominal aortic aneurysm (AAA) by providing two aortic vascular conduit devices 100b (see FIG. 7) for example connected by a section of conduit 1020 spanning the diseased and/or damaged portions of the abdominal aorta.

As discussed below, the flexible flange 13 and tube 1 of various embodiments of the vascular conduit device 100 may be altered so as to be compatible with various tissue walls 850. For example, the vascular conduit device 100 shown in FIG. 7 may be suited for use in defining and maintaining an aperture in a large blood vessel having a curved tissue wall (such as the aorta). Furthermore, the vascular conduit device 100 shown in FIG. 6 may be suited for use in defining and maintaining an aperture in a body cavity having a relatively thick and/or muscular tissue wall (such as the cardiac muscle of the left ventricle).

Therefore, as shown in FIG. 7, the flexible flange 13 may define, in some embodiments, a convex profile with respect to the proximal end 7 of the tube 1 so as to be capable of conforming to a curved first tissue surface 853 (such as a tissue surface defined by the inner wall surface of a blood vessel (such as the aorta)). Furthermore, in some embodiments, the securing ring 17 may also include a flange 630 defining a corresponding concave profile such that the securing ring 17 may be capable of operably engaging a curved and/or contoured second tissue surface 855 and be better capable of cooperating with the flexible flange 13 so as to secure the vascular conduit device 100 within the aperture 800. Furthermore, as shown generally in FIG. 6, the flexible flange 13 may also comprise a frusto-conical assembly such that the insertion of the flexible flange 13 into a relatively narrow tissue aperture 800 may be more easily accomplished (see generally FIG. 8A). Furthermore, the frusto-conical assembly of some flexible flange 13 embodiments of the present invention may also prevent and/or minimize the occurrence of the accidental removal of the vascular conduit device 100 from the second tissue surface 855 of the tissue wall 850. The relative thicknesses of the materials used to form the flexible flange 13 may also be varied so as to allow the flange 13 to be optimized based on the expected type of tissue wall 850 it may be used to engage. For example, a relatively thin and/or contoured flexible flange 13 (as shown generally in FIG. 7) may be used to secure vascular conduit devices 100 within more fragile and/or thin blood vessels. Furthermore, the relatively thick and robust frusto-conical flexible flange 13 (shown generally in FIG. 6) may be used to secure vascular conduit devices 100 within more substantial tissue walls (such as cardiac muscle).

Tube 1 and flange 13 may be made-of any suitable biocompatible material. Alternatively, tube 1 and flange 13 may be coated with a biocompatible material. According to one exemplary embodiment, the tube 1 may comprise a first polymer material having a first hardness and the flange 13 may comprise a second polymer material having a second hardness, wherein the first hardness is greater than the second hardness. Thus, according to some such embodiments, the flange 13 may be easily deformable as it is inserted into the aperture 800 defined in the tissue wall 850, but the tube 1 may remain relatively rigid so as to maintain a path for fluid communication (see element 860, FIG. 8B) between the surfaces 853, 855 of the tissue wall 850.

According to some other embodiments, at least a portion of the outer surface 9 of tube 1 may be threaded. Threading 15 may extend the entire length of tube 1, or extend over only a portion thereof. According to one exemplary embodiment, threading 15 may be absent from a length of the distal end 5 of the tube 1 that is slightly less than the thickness of the tissue wall 850. This alternative embodiment may serve to prevent over-tightening of the vascular conduit device 100, which may, in some case lead to damage and/or rupture of portions of the tissue wall 850 near the aperture 800 defined therein. According to another embodiment, threading 15 may not extend all the way to the proximal end 7 such that the tube 1 (and the resulting vascular conduit device 100) may be used to provide a conduit through tissue walls having a variety of thicknesses.

External ring 17 (or securing ring 17) may be provided with an inner diameter 18 and an outer diameter 19. Inner diameter 18 may further define threads 23 to correspond to the threading 15 on the outer surface 9 of tube 1. The outer diameter 19 of external ring 17 may have any shape suitable to the designer, including circular or hexagonal. According to one embodiment of the invention, external ring 17 may be adapted to be engaged by a tightening device (not shown) for tightening external ring 17 on tube 1. As discussed above with respect to the tube 1, the external ring 17 may be made of any suitable biocompatible material. Alternatively, external ring 17 may be coated with a biocompatible material.

Figure 11:
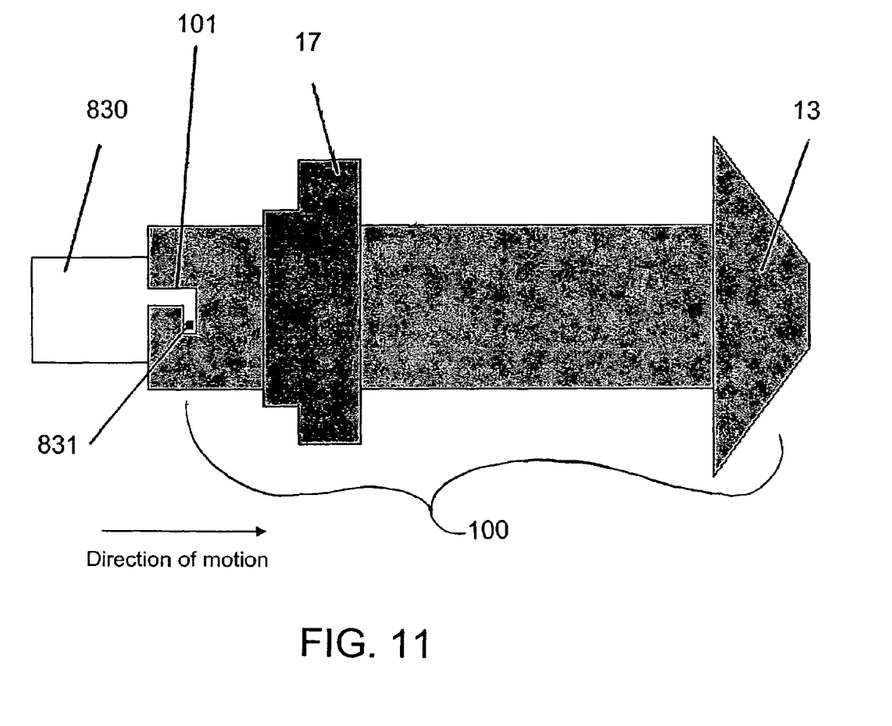
FIG. 11 is a side view of an exemplary embodiment of the conduit device of the present invention including a notch and pin arrangement for selectively engaging the conduit device with a coring device.

For embodiments wherein the tube defines threading 15 and wherein the complementary external ring 17 defines threads 23, the tightening device may comprise a specialized wrench device for rotating the external ring 17 relative to the tube 1. Furthermore, in other embodiments (such as those shown generally in FIGS. 6 and 7) the tightening device may comprise a simple push tool capable of encircling a coring device 830 (see discussion below of FIG. 8A) and pushing the external ring 17 towards the distal end 5 of the tube 1 such that the at least one pawl member 620 of the external ring 17 may be engaged with the plurality of ridges 610 defined on an outer surface of the tube 1. According to some embodiments of the present invention, as shown generally in FIG. 11, the vascular conduit device 100 may be selectively secured to the coring device 830 (or, in some embodiments, the delivery device 910, discussed below) by a pin 831 and notch 101 arrangement. For example, as shown in FIG. 11 a pin 831 may extend from an external surface of the coring device 830 (or the delivery device 910) and be operably engaged with a complementary notch 101 defined in the proximal end of the vascular conduit device 100. Thus, a clinician may use the coring device 830 (or the delivery device 910) to advance the vascular conduit device 100 to the aperture 800 and into an implanted position (see FIG. 8B, for example) and subsequently apply counter-traction to the vascular conduit device 100 (via the pin 831) such that the external ring 17 may be advanced and secured relative to the vascular conduit device 100. In some embodiments, the clinician may then rotate the coring device 830 (and/or the delivery device 910) to release the pin 831 from the notch 101 and retract the coring device 830, leaving the vascular conduit device 100 securely implanted (as shown generally in FIG. 8B). Furthermore, in some embodiments, the hemostatic device 820 (see FIG. 8A) may also be used to apply counter-traction force to hold the tube 1 and flexible flange 13 in place within the aperture 800 as the external ring 17 is engaged with respect to the second tissue surface 855 from a proximal position.

Figure 3:
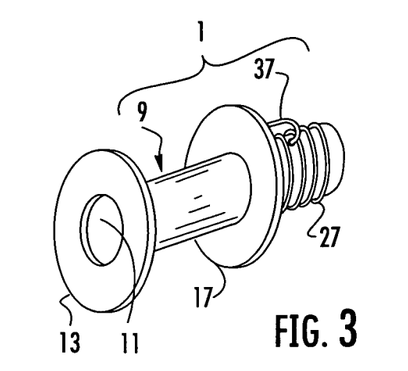
FIG. 3 is a perspective view oft second embodiment of an LV apical connector according to the invention.
Figure 4:
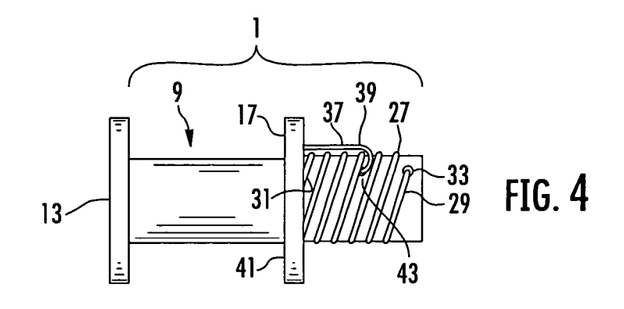
FIG. 4 is a side view of the embodiment shown in FIG. 3.
Figure 5:
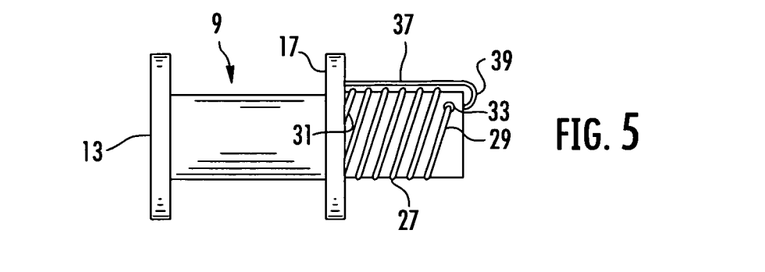
FIG. 5 is aside view of a third embodiment of an LV apical connector according to the invention.

According to the embodiment shown in FIGS. 3 and 4, tube 1 of the vascular conduit device 100 may also be provided with an external ring 17 that is biased toward flange 13 by a biasing device 27 (such as a spring device), having proximal end 29 and distal end 31. The biasing device 27 may be configured so as to tend to force external ring 17 into contact with flange 13. As shown in FIGS. 4-6, the biasing device 27 may be a spring in compression. As one of ordinary skill in the art will appreciate, any biasing device may be used, including one or more flexible bands or rods. Furthermore, tube 1 may be provided with and/or define an engagement feature 33, such as a ring, slot or bore, to engage the proximal end 29 of the biasing device 27. Likewise, external ring 17 may be provided with an engagement feature (not shown) adapted to receive the distal end 31 of the biasing device 27.

According to some embodiments, release device 37 may also be provided to releasably hold external ring 17 and biasing device 27 in pre-deployment configuration, with biasing device 27 in compression, until such a time as the flange 13 has been placed in the interior of a cavity defined by the tissue wall 850 (such as the interior of the ventricle) and the external ring 17 is ready to be deployed against the outer tissue surface 855 of the heart muscle (see generally FIG. 8B, showing the vascular conduit device 100 secured within the aperture 800).

According to the embodiment shown in FIGS. 1 and 4, release device 37 may include one or more hooks 39 extending from the proximal surface 41 of the external ring 17 and adapted to releasably engage an engagement feature 43; for example, a slot or bore, defined in tube 1. Alternatively, as shown in FIG. 5, the release device 37 may extend to and hook over the proximal end 7 of tube 1.

In some additional embodiments, a portion of tube 1 may be threaded and the inside diameter of external ring 17 threaded to permit further tightening of external ring 17 on tube 1 after deployment of the external ring 17 following removal of the release device 37.

Some embodiments of the present invention, as shown generally in FIG. 8A, further provide a system for implanting a vascular conduit device 100, wherein the system comprises a coring device 830 for defining an aperture 800 in a tissue wall 850 having a first tissue surface 853 and a second tissue surface 855. The various components of the system embodiments of the present invention may be inserted into a patient (via, for example, a thoracoscopic, endovascular, and/or percutaneous procedure) such that a guide catheter (not shown) and/or guide wire 810 (see FIG. 8B) may be inserted into the thoracic cavity of a patient in order to gain access to diseased vasculature and/or the heart. Furthermore, according to some embodiments, the system of the present invention may be used to implant a vascular conduit device 100 via more invasive surgical procedures that will be appreciated by one skilled in the art. Furthermore, as shown generally in FIG. 12, the vascular conduit device 100 may also be delivered and implanted endovascularly from the inside (and/or from a first tissue surface 853) of the ventricle and/or aorta.

As shown in FIG. 8A, the coring device 830 may define a lumen adapted to be capable of receiving a guide wire 810 for directing the coring device 830 to the second tissue surface 855. Furthermore, the system of the present invention may also comprise a conduit device 100 (such as the vascular conduit device discussed above) for lining the aperture 800 defined in the tissue wall 850 and maintaining fluid communication between the first 853 and second tissue 855 surfaces of the tissue wall 850. The conduit device 100 may be adapted to be capable of being advanced over the guide wire 810 and coring device 830. As described above with respect to FIGS. 1-5, the vascular conduit device 100 may comprise: a tube 1 having proximal 7 and distal 5 ends, and inside and outside surfaces; a flexible flange 13 disposed at or near the distal end 5; and a securing ring 17 (or external ring 17) adapted to fit over the tube 1 and adapted to be capable of operably engaging the second tissue surface 855 and cooperating with the flexible flange 13 so as to secure the conduit device 100 within a tissue aperture 800.

According to various embodiments of the system of the present invention, the coring device 830 may comprise at least one of: a pulsed laser scalpel; a continuous wave laser scalpel; a mechanical coring device (such as, for example, a rotoblator catheter or other mechanical and/or catheter-based mechanical cutting device); an ultrasonic coring device (such as high-frequency focused ultra-sound); and combinations thereof. For example, in one exemplary embodiment, the coring device 830 may comprise a pulsed excimer laser device having a light pulse duration that is less than the tissue wall's 850 time of thermal diffusion (defining how quickly the laser's imparted heat spreads to adjacent tissue) so as to provide a relatively "cool" cutting method (i.e. less than about 50 degrees C.). Furthermore, the pulsed laser may be provided with a relatively shallow cutting depth (i.e. less than about 50 µm) such that the coring device 830 may be precisely controlled. The use of a pulsed laser scalpel as the coring device 830 may thus result in minimal damage to tissue adjacent the targeted aperture 800 area, which may be especially advantageous in embodiments wherein the system is used to implant a vascular conduit device 100 in the ventricular apex, as the cardiac tissue of the left ventricle contains tissues that are vital for maintaining the electrical pacing of the heart.

Some system embodiments of the present invention (as shown generally in FIG. 8A) may further comprise a hemostatic device 820 for selectively deploying so as to temporarily occlude the aperture 800. As one skilled in the art will appreciate, the hemostatic device 820 may be adapted to be capable of being advanced over the guide wire 810 within the lumen of the coring device 830. Furthermore, according to some embodiments, the hemostatic device 820 may be delivered via a delivery catheter defining a lumen for receiving the guide wire 810 and having a sufficiently small outer diameter to be guided within the lumen defined by the coring device 830. According to various embodiments of the present invention, the hemostatic device 830 may comprise at least one of: an "umbrella" occlusion device; a dilation balloon; and/or combinations thereof. According to some embodiments, the hemostatic device 820 (as shown in FIG. 8A) may be used to maintain "traction" for the advance of the coring device 830 (which, in pulsed excimer laser embodiments, may comprise a circular array 835 of lasers that must be advanced into the tissue wall 850 in order to core the wall and define an aperture 800 therein). Thus, in some embodiments, a clinician may deploy the hemostatic device 820 proximal to the first tissue surface 853 of the tissue wall 850 and exert a force (using the deployed hemostatic device) against the first tissue surface 853 such that the laser array 835 of the coring device 830 may be advanced to define the aperture 800 in the tissue wall 850. The exertion of such "traction" forces using the hemostatic device 820 may be useful in instances wherein the tissue wall 850 is in motion (such as is the case with the cardiac muscle defining the walls of the left ventricle). Thus, embodiments of the present invention may be successfully employed in "off-pump" procedures wherein the heart is left beating during the course of the procedure for implanting the vascular conduit device 100.

Following the coring process, the vascular conduit device 100 (as described in its various embodiments above) may be advanced along the outer surface of the coring device 830 and into position within the aperture (as shown generally in FIG. 8B) so as to define a pathway for fluid flow 860 through the tissue wall 850. According to some embodiments, a dilator device (not shown) may be introduced (over the guide wire 810, for example) for dilating the initial aperture 800 defined by the coring device 830. The dilator device may also be used to advance the vascular conduit device 100 into its final implanted position (see FIG. 8B) by at least partially expanding the dilator device within the inner surface 11 of the tube 1 so as to carry the vascular conduit device 100 with the partially-expanded portion of the dilator device. The dilator device may comprise, in various embodiments, a dilation balloon, a multi-arm endoscopic and/or thoracoscopic retractor device, and/or other types of dilator devices that will be appreciated by one skilled in the art.

Figure 9A:
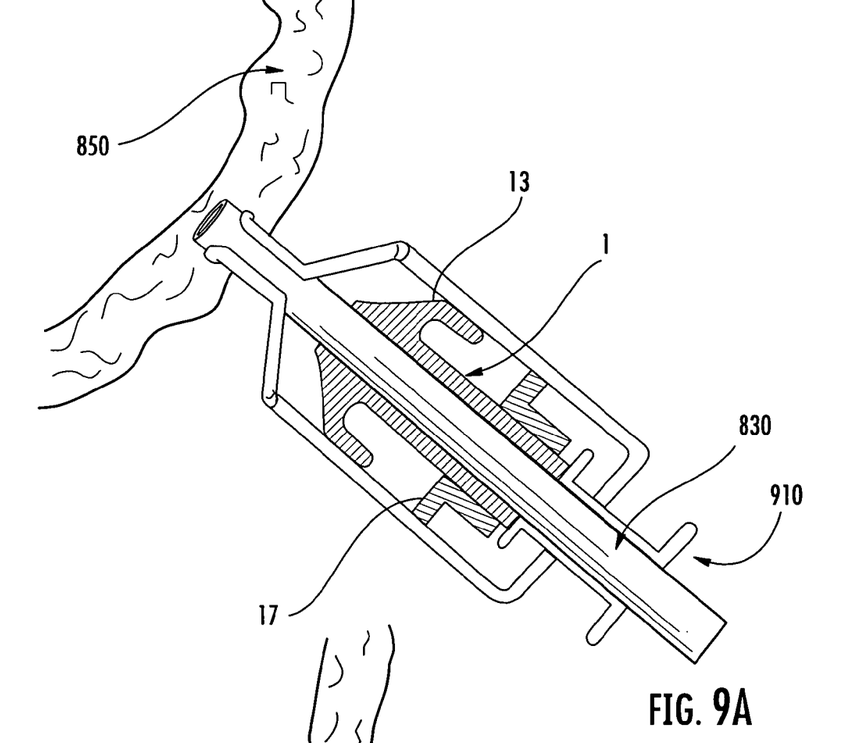
FIG. 9A is a cross-sectional side view of a system according to one embodiment of the present invention including a delivery device for enclosing and selectively delivering the conduit device.
Figure 9B:
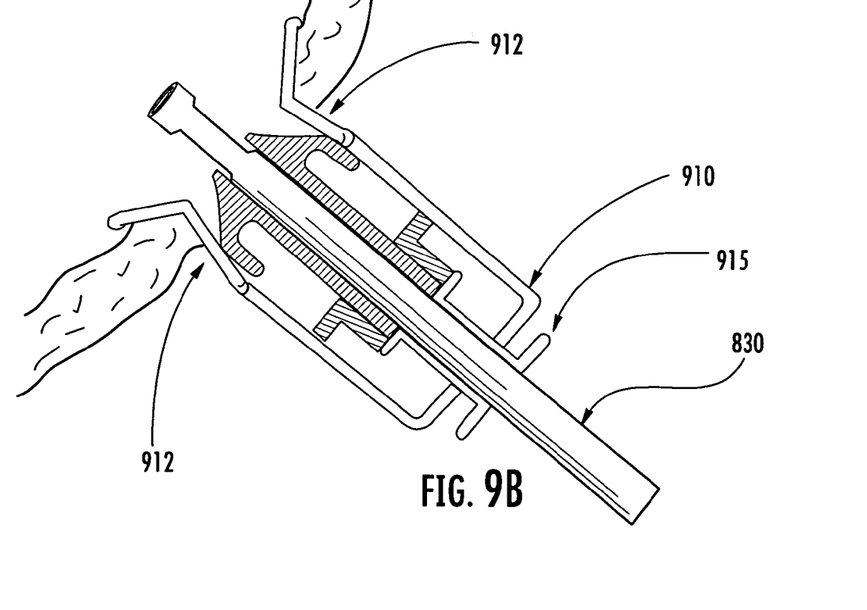
FIG. 9B is a cross-sectional side view of a system according to one embodiment of the present invention including a delivery device comprising a pair of retracting arms for dilating the aperture during implantation of the conduit device.

For example, as shown generally in FIGS. 9A and 9B, some embodiments of the present invention may comprise a dilator device that may serve as a delivery device 910 for dilating the aperture 800 formed by the coring device 830 and for percutaneously and/or thoracoscopically delivering the vascular conduit device 100 to a secured position (see FIG. 8A, for example) relative to the aperture 800 defined in the tissue wall 850. The delivery device 910 may be operably engaged with an outer surface of the coring device 830 and may comprise two or more retractor arms 912 that may be opened as the vascular conduit device 100 is pushed out from the delivery device 810 by applying an opening force to a plunger 915. Thus, as shown in FIG. 9B, the delivery device 910 may be configured to simultaneously dilate the aperture 800 (using the retractor arms 912) and deliver the vascular conduit device 100. As shown in FIG. 9B the flexible flange 13 of the vascular conduit device 100 may urge the retractor arms 912 to an open position as the plunger 915 pushes the vascular conduit device 100 outward and into the aperture 800. The retractor arms 912, when deployed as shown in FIG. 9B may also serve to provide "counter-traction" such that the clinician may apply a distally-acting force on the plunger 915, a clinician may deploy the securing ring 17 relative to the tube 1 of the vascular conduit device 100 in order to secure the vascular conduit device 100 within the aperture 800 (as shown in FIG. 8B, for example).

As described above (see FIG. 8A, for example) the hemostatic device 820 may also be deployed in order to provide additional "counter-traction" such that the distal end of the vascular conduit device 100 (once implanted in the aperture 800) may contact the expanded hemostatic device 820. Thus, by applying a distally-acting force on the plunger 915, a clinician may deploy the securing ring 17 relative to the tube 1 of the vascular conduit device 100 in order to secure the vascular conduit device 100 within the aperture 800 (as shown in FIG. 8B, for example).

According to one exemplary embodiment, the system of the present invention (shown generally in FIGS. 8B and 10) may be used to implant vascular conduit devices 100a, 100b to serve as the terminal points for an apico-aortic conduit. According to such embodiments, a thoracoscopic procedure may be used to insert a needle through the apex and into the left ventricle 850a. A guide wire 810 may then inserted into the opening and, following dilation of the opening (using a dilation device, for example), an hemostatic device 820 may be threaded over the wire 810 and into the left ventricle and deployed proximal to an first tissue surface 853 thereof. The hemostatic device 820 may comprise, for example, known occlusion devices such as an occlusion balloon, the Guidant Heartstring™, or the Baladi inverter, disclosed in U.S. Patent Nos. 5,944,730 and 6,409,739. As described above, and as shown generally in FIG. 12, the vascular conduit devices 100a, 100b may also be implanted endovascularly (i.e. from the inside of the left ventricle and/or the aorta) by introducing the system embodiments of the present invention through the vasculature via guidewire and/or guiding catheter. For example, the aortic conduit 100b may be introduced via the system embodiments of the present invention (including a guiding catheter) inserted in the femoral artery. In addition, the ventricular conduit 100a may be introduced via the systems of the present invention (including a guiding catheter) inserted into the femoral vein, across the atrial septum, through the mitral valve and out the ventricular free wall.

A ventricular coring device 830 may then be threaded in-line over the hemostatic device 820 and a core of ventricular muscle is removed from the tissue wall 850 of the apex in order to form an aperture 800. In addition to known coring techniques, an annular contact laser (and in some embodiments a "cool" cutting pulsed excimer laser, having elements arranged in a circular array 835) may be used to vaporize the tissue along the perimeter of the core. The cored tissue may then be removed according to known methods. According to a further alternative embodiment, a contact laser may be used to vaporize the entire area of the core, eliminating the need to remove cored tissue. In yet another embodiment, a mechanical coring device (such as a catheter-based rotoblator device) or an ultrasonic coring device, may be used to form the aperture 800. No matter the method of coring, once coring has been-completed, the coring device 830 may be removed while the occlusion device maintains hemostasis, and the vascular conduit device 100 of the present invention may be mounted on a dilator and-introduced over the guide wire 810 and hemostatic device 820. As the vascular conduit device 100 is introduced into the aperture 800 in the apex, the flexible flange 13 may deform and/or retract. As the vascular conduit device 100 enters the-left ventricle, it may displace the hemostatic device 820 to allow the flexible flange 13 to resume its normal shape. As discussed above the vascular conduit device 100 may then be drawn tight against the first tissue surface 853 of the wall 850 of the left ventricle. According to a first embodiment, external ring 17 is threaded onto the tube 1 and tightened until it is snug against the second tissue surface 855 of the ventricular apex.

According to it second embodiment, once the flexible flange 13 has been introduced into the ventricle and pulled back to engage the first tissue surface 853, release-device 37 is released, allowing biasing device 27 to force the external ring 17 against the second tissue surface 855 of the ventricular apex. According to a further aspect of this embodiment of the invention, threads on the inside diameter of external ring 17 may be made to engage threads on the outer surface of the tube 1 to further secure external ring 17 against the tissue wall 850 of the ventricular apex.

Once the vascular conduit device 100 is firmly in place (see generally FIG. 8B), the occlusion device 820 may be retracted and withdrawn. The vascular conduit device 100 may then be clamped shut and/or capped while its free end (defined by the proximal end 7 of the tube 1) is connected to a valved conduit and/or graft which may terminate at a complementary vascular conduit device 100 implanted in the aorta (see FIG. 7 showing an exemplary embodiment of a vascular conduit device 100 suited for implantation in the tissue wall 850 of the aorta).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for implanting a vascular conduit device, the system comprising:
    a coring device for defining an aperture in a tissue wall having a first tissue surface and a second tissue surface, the coring device defining a lumen adapted to receive a guide for directing the coring device to the second tissue surface;
    an articulating device for selectively deploying through the tissue wall and proximate the first tissue surface, the articulating device adapted to provide counter-traction for advancing the coring device into the tissue wall and to selectively occlude the aperture;
    a sutureless conduit device for lining the aperture and maintaining fluid communication between the first and second tissue surfaces of the tissue wall, the sutureless conduit device adapted to be separably positioned over and coaxial with the coring device and to be advanced over the coring device and into the aperture, the sutureless conduit device comprising a tube having proximal and distal ends, and inside and outside surfaces, the inside surface of the tube adapted to slidably contact an outer surface of the coring device when the sutureless conduit device is positioned over the coring device; and
    a delivery device for selectively deploying the sutureless conduit device into the aperture, the delivery device comprising a plurality of retractor arms adapted to engage the tissue wall and to provide counter-traction for advancing the sutureless conduit device into the aperture.

2. The system according to claim 1, wherein the coring device is selected from the group consisting of:
    a pulsed laser scalpel;
    a continuous wave laser scalpel;
    a mechanical coring device;
    an ultrasonic coring device; and
    combinations thereof.

3. The system according to claim 1, wherein the articulating device comprises an umbrella occlusion device.

4. The system according to claim 1, wherein the sutureless conduit device is further adapted to implant a ventricular assist device in the tissue wall.

5. The system according to claim 1, wherein the sutureless conduit device further comprises at least one flexible flange disposed at or near the distal end of the tube, the flexible flange having a larger outer diameter than the tube and adapted to operably engage the first tissue surface.

6. The system according to claim 5, wherein the flexible flange has a frusto-conical shape.

7. The system according to claim 5, wherein the flexible flange is adapted to deform sufficiently to allow the distal end of the tube and the flange to be inserted through the aperture defined in the tissue wall, the aperture having a diameter equal to or less than the diameter of the tube.

8. The system according to claim 7, wherein the flexible flange has sufficient shape memory that once deformed to allow insertion of the distal end of the tube and the flange through the aperture, the flange will return to a larger original shape.

9. The system according to claim 5, wherein the flexible flange extends about an entire circumference of the tube.

10. The system according to claim 1, wherein the sutureless conduit device is further adapted for the passage of medical or surgical instruments during an intervention through the tissue wall.

11. The system according to claim 1, further comprising a guiding wire or a guiding catheter for directing the coring device and the sutureless conduit device to the tissue wall via an endovascular pathway.

12. The system according to claim 1, wherein a proximal end of the sutureless conduit device is operably engaged with the coring device.

13. The system according to claim 1, wherein the delivery device further comprises a plunger adapted to be slidably disposed with respect to the coring device and to advance the sutureless conduit device over the coring device and into the aperture, and wherein the retractor arms are adapted to engage the tissue wall while the plunger advances the conduit device over the coring device and into the aperture.

14. The system according to claim 13, wherein the retractor arms are adapted to dilate the aperture while the plunger advances the conduit device over the coring device and into the aperture.

15. The system according to claim 1, further comprising a valve adapted to control fluid flow through the sutureless conduit device.

16. The system according to claim 15, wherein the valve is adapted for the passage of medical or surgical instruments.

17. The system according to claim 1, wherein the articulating device is adapted to be advanced over the guide and within the lumen of the coring device.

18. The system according to claim 1, wherein the articulating device is adapted to be advanced over the guide and within the lumen of the sutureless conduit device.

19. The system according to claim 1, wherein the retractor arms are adapted to dilate the aperture.

20. The system according to claim 1, wherein the retractor arms are flexible.

21. The system according to claim 1, wherein the retractor arms are adapted to move from a closed position to an open position as the sutureless conduit device is advanced over the coring device and into the aperture.

22. The system according to claim 1, wherein the sutureless conduit device is adapted to move the retractor arms from a closed position to an open position as the sutureless conduit device is advanced over the coring device and into the aperture.

23. The system according to claim 1, wherein the retractor arms extend over the sutureless conduit device.

24. A system for implanting a vascular conduit device, the system comprising:
- a coring device for defining an aperture in or near a ventricular apex of a heart tissue wall having an inner first tissue surface and an outer second tissue surface, the coring device defining a lumen adapted to receive a guide for directing the coring device to the second tissue surface, the coring device adapted to remove and capture a core of tissue from the heart tissue wall to define the aperture;
- an articulating device for selectively deploying through the heart tissue wall and proximate the first tissue surface, the articulating device adapted to provide a hemostatic surface about the first tissue surface when the articulating device is in an expanded configuration, to provide counter-traction for advancing the coring device into the heart tissue wall and to selectively occlude the aperture;
- a sutureless conduit device for lining the aperture and maintaining fluid communication between the first and second tissue surfaces of the heart tissue wall, the sutureless conduit device adapted to be separably positioned over and coaxial with the coring device and to be advanced over the coring device and into the aperture, the sutureless conduit device comprising:
  - a tube having proximal and distal ends, and inside and outside surfaces, the inside surface of the tube adapted to slidably contact an outer surface of the coring device when the sutureless conduit device is positioned over the coring device;
  - a flexible flange disposed at or near the distal end of the tube, the flexible flange having a frusto-conical shape expanding from a distal end to a proximal end thereof, the flexible flange adapted to deform sufficiently to be inserted through the aperture and to operably engage the first tissue surface; and
  - a securing ring adapted to selectively engage the outer surface of the tube and to advance over the tube to operably engage the second tissue surface so as to secure the sutureless conduit device in the aperture; and
- a delivery device for selectively deploying the sutureless conduit device into the aperture, the delivery device comprising:
  - a plurality of retractor arms adapted to engage the tissue wall and to provide counter-traction for advancing the sutureless conduit device into the aperture; and
  - a plunger adapted to advance the sutureless conduit device over the coring device and into the aperture.

25. The system according to claim 24, wherein the sutureless conduit device is further adapted to implant a ventricular assist device in the tissue wall.

26. The system according to claim 24, wherein the retractor arms are adapted to engage the tissue wall while the plunger advances the sutureless conduit device over the coring device and into the aperture.

27. The system according to claim 24, wherein the articulating device comprises an umbrella occlusion device.

28. The system according to claim 24, further comprising a valve adapted to control fluid flow through the sutureless conduit device.

29. The system according to claim 28, wherein the valve is adapted for the passage of medical or surgical instruments.

30. A system for implanting a vascular conduit device, the system comprising:
- a coring device for defining an aperture in a tissue wall having a first tissue surface and a second tissue surface, the coring device defining a lumen adapted to receive a guide for directing the coring device to the second tissue surface, the coring device adapted to remove and capture a core of tissue from the tissue wall to define the aperture;
- a sutureless conduit device for lining the aperture and maintaining fluid communication between the first and second tissue surfaces of the tissue wall, the sutureless conduit device adapted to be separably positioned over and coaxial with the coring device and to be advanced over the coring device and into the aperture, the sutureless conduit device comprising a tube having proximal and distal ends, and inside and outside surfaces, the inside surface of the tube adapted to slidably contact an outer surface of the coring device when the sutureless conduit device is positioned over the coring device; and
- a delivery device for selectively deploying the sutureless conduit device into the aperture , the delivery device comprising:
  - a plurality of retractor arms adapted to engage the tissue wall and to provide counter-traction for advancing the sutureless conduit device into the aperture; and
  - a plunger adapted to advance the sutureless conduit device over the coring device and into the aperture.

31. A system for implanting a vascular conduit device, the system comprising:
- a coring device for defining an aperture in or near a ventricular apex of a heart tissue wall having a first tissue surface and a second tissue surface, the coring device adapted to be advanced over a guidewire and to remove a core of tissue from the heart tissue wall to define the aperture;
- a sutureless conduit device for lining the aperture and maintaining fluid communication between the first and second tissue surfaces of the heart tissue wall, the sutureless conduit device adapted to be advanced over the coring device and into the aperture;

a valve adapted to control blood flow through the sutureless conduit device; and a delivery device for selectively deploying the sutureless conduit device into the aperture, the delivery device comprising a plurality of retractor arms adapted to engage the tissue wall and to provide counter-traction for advancing the sutureless conduit device into the aperture.

\* \* \* \* \*